United States Patent [19]

Convers et al.

[11] Patent Number: 4,460,699

[45] Date of Patent: Jul. 17, 1984

[54] FIXED BED CATALYST FOR OXYCHLORINATION

[75] Inventors: Ronald J. Convers; Robert M. Owens, both of Ponca City, Okla.

[73] Assignee: Conoco Inc., Ponca City, Okla.

[21] Appl. No.: 405,133

[22] Filed: Aug. 4, 1982

[51] Int. Cl.³ .................. B01J 23/02; B01J 23/34; B01J 23/72; B01J 23/74

[52] U.S. Cl. ........................... 502/84; 502/80; 502/170; 502/201; 502/218; 502/224; 502/225; 502/229; 502/244; 502/340; 502/345; 502/346; 502/439; 570/243; 570/245

[58] Field of Search .............. 252/442; 570/243, 245; 502/170, 201, 218, 224, 225, 229, 244, 340, 345, 346, 439, 80, 84

[56] References Cited

U.S. PATENT DOCUMENTS

| | | | |
|---|---|---|---|
| 3,427,359 | 2/1969 | Rectenwald et al. | 570/245 |
| 3,564,066 | 2/1971 | Trebillon et al. | 570/245 |
| 3,839,224 | 10/1974 | Yonehara et al. | 252/466 PT |
| 3,892,816 | 7/1975 | Kister | 570/245 |
| 4,206,180 | 6/1980 | Campbell et al. | 422/190 |

FOREIGN PATENT DOCUMENTS

1548303 7/1979 United Kingdom .

*Primary Examiner*—W. J. Shine
*Attorney, Agent, or Firm*—Robin M. Davis

[57] ABSTRACT

The present invention provides a fixed bed catalyst for the oxychlorination of ethene, alpha olefins and aromatics. More specifically, this invention relates to a catalyst having an impeded center which excludes reactants, or prevents products from forming in the interior of the catalyst. The impeded center may be made inaccessible or it may be inert to reaction. Thin layers of high specific surface area carrier material cover the outer surface of the impeded center. An agent capable of catalyzing oxychlorination reactions is added to the layered catalytic carrier material.

9 Claims, 5 Drawing Figures

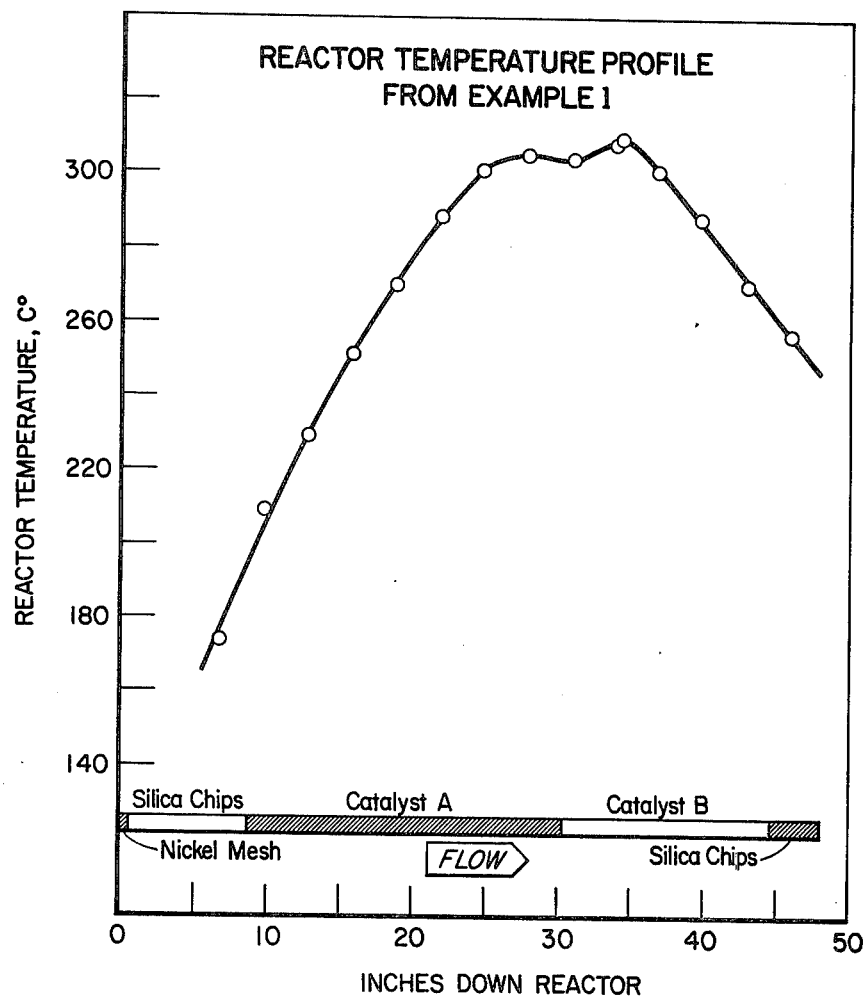

FIXED BED CATALYST FOR OXYCHLORINATION

DESCRIPTION

TECHNICAL FIELD

The present invention relates to catalysts for the oxidative chlorination of olefins and aromatic compounds. The production of chlorinated hydrocarbons by oxidative chlorination of hydrocarbons is well known in the art. The process normally consists of catalytically reacting olefinic or aromatic hydrocarbons, hydrogen chloride, and oxygen. Hydrogen chloride is employed as a source of chlorine for the hydrocarbon which is the chlorine acceptor in the reaction thereby producing chlorinated hydrocarbons as the product.

BACKGROUND AND SUMMARY OF THE INVENTION

Representative but nonexhaustive examples of art in this area include U.S. Pat. No. 4,123,467, which describes a catalyst comprising a spherical, high surface area, activated alumina impregnated with the catalytic agent, copper chloride, and the modifier, potassium chloride. The process described in this patent utilizes catalyst beds in two sections, with the more active catalyst in the lower section.

Other U.S. patents describe catalysts made by impregnating carrier material with catalytic material. These catalysts are useful in fixed bed operations, but are more suited for fluid bed operations. U.S. Pat. No. 4,172,052 describes a catalyst prepared by treating particulate carrier material with aluminum halide, copper halide, and optionally an alkali metal halide. Impregnation may be carried out in either one step with a single aqueous solution, or in several steps with aqueous solutions of the single reagent which is to be loaded onto the solid carrier. U.S. Pat. No. 4,123,389 describes a catalyst wherein the carrier is formed from colloidal sized particles adhering to each other in structures resembling chains and loops. The carrier employed has a low bulk density, a surface area of a minimum 50 square meters per gram, and nonporous particles with pore diameters in the range of 50 to 1,000 Angstroms. Impregnation with the active catalyst ingredients is carried out in steps so that there is a first layer or deposit of copper chloride which is partially covered with a second layer of at least one alkali metal chloride.

U.S. Pat. No. 3,427,359 describes a catalyst prepared from a carrier having a high pore volume and low surface area, but is more suitable for a fluid bed system.

None of these prior art catalysts are entirely satisfactory, whether used in fluidized bed or fixed bed processes. Fluidized bed reactor processes are much more difficult to operate on a commercial basis. The catalysts used in those processes tend to suffer severe attrition, and must be continuously replaced. The fixed bed process, on the other hand, has disadvantages such as activity control.

Another disadvantage found in the production of chlorinated aliphatic and aromatic hydrocarbons by oxychlorination are the undesired by-products produced in the reaction. In ethylene oxychlorination a major by-product is ethyl chloride. Coke is responsible for catalyst deactivation and fracturing, which accelerates the need to replace the catalyst.

It would therefore be of great benefit to provide a catalyst which provides the advantages of a fixed bed catalyst process, is capable of improved selectivity to the desired product, has longer catalyst life, and provides better activity control. It is an object of the present invention to provide an improved fixed bed catalyst which is more selective to desired oxychlorination products, has a long life, and improved activity control. Other objects will become apparent to those skilled in the art as this description proceeds.

The present invention provides a structured catalyst which, in addition to offering the advantages inherent to a fixed bed catalyst, requires less active catalytic material per gram, is more selective to desired products, delivers excellent activity control with/or without the use of modifiers or physical catalyst diluents, and has a longer catalytic life because of less coke formation. Specifically, this catalyst comprises a structured catalyst for oxychlorination of ethylene, alpha olefins, and aromatics comprising: (a) an impeded center; (b) a layer of catalyst carrier material having a thickness in the range of about 0.001 millimeters to 1 millimeter disposed on (a); (c) a catalytic agent for oxychlorination disposed on or dispersed in the layer of catalyst carrier material in an amount that said catalytic agent is present at a concentration of from about 0.01 to 20% (by wt.) of the finished catalyst.

In this invention the "impeded" center is a center which prevents the oxychlorination reaction due to physical inaccessibility of the center and/or due to the absence of catalytic sites in the central portions of the catalyst. The absence of these necessary sites may be insured by the exclusion of the catalyst carrier material or the catalytic agent, since it is the union of the proper catalyst carrier material with the catalytic agent for oxychlorination that creates active sites which promote the reaction. Since the center area of the structured catalyst of the present invention is, by its inert character and/or its inaccessibility, excluded from the oxychlorination reaction, the reaction is forced to take place in the layered carrier material. Conditions in this layered area insure better diffusivity and higher concentrations of reactants. This arrangement encourages production of desired oxychlorination products. This is at the direct expense of by-products, (such as ethyl chloride in the case of ethylene), since by-product formation preferentially takes place toward the central area of the conventional fixed bed oxychlorination catalyst. The catalysts of the present invention are therefore more selective to desired products.

Coke formation also occurs preferentially in the central areas of the usual fixed bed oxychlorination catalyst. Impeded centers inside the catalysts of the present invention exclude coke-forming reactions in these areas, thus increasing catalyst life.

Oxychlorination activity is controlled without resorting to conventional methods such as catalyst modifiers or physical catalyst diluents such as graphite, clay, or $SiO_2$, although these may be used also if an additional control parameter is desired. Control is achieved, with or without accompanying conventional methods, by varying the depth of the layered catalytic carrier to specifically desired amounts, thereby inducing the desired change in activity. The structured nature of the present invention decreases, if not virtually eliminates, hot spot problems in commercial reactors.

DETAILED DESCRIPTION OF THE INVENTION

The structured catalysts of the instant invention have an impeded center. The type of material used for this center is not critical provided that it is stable under oxychlorination reaction conditions. This center is inaccessible to reactants and/or inert for reaction due to the substantial absence of catalytic sites. This effectively eliminates the reaction from the interior volume, and is done through the catalyst preparation method, or by having a center with a low specific surface area and/or a low porosity. A layered catalyst carrier material covers the impeded center and can be used to make the center inaccessible to reactants. The oxychlorination reaction takes place in this carrier layer. The thickness of this layer may vary between 0.001 mm and 1 mm. The catalyst is completed by any catalytic agent capable of promoting oxychlorination. This agent is either dispersed in, or preferably, is placed on the layer of catalytic carrier material. The amount of catalytic agent added to the surface of this structured catalyst is not critical. Generally any amount practical for the catalysis of the oxychlorination reaction is used. Such a range would be from about 0.1 to about 20% by weight based on the weight of the finished catalyst.

The reactant feed material which may be used with these catalysts are ethylene, alpha olefins, and aromatics. Representative but nonexhaustive examples of the alpha olefin feed are propene, butene, and pentene. An example of the aromatic feed which is preferred is benzene. The most preferable olefinic feed for this reaction is ethylene.

It should be noted that these catalysts are especially successful with regard to ethylene oxychlorination. Reduced ethyl chloride formation, and increased concentrations of ethylene di chloride (EDC) and carbon tetrachloride have been noted. This is desirable since $CCl_4$ is a useful initiator when combined with ethylene di chloride (EDC) in the production of vinyl chloride.

The shape of the impeded center will largely determine the geometric shape of the overall finished catalyst. Any geometric shape capable of use in a fixed bed system is suitable. Particulate shaped impeded centers may even be hollow as long as the center is truly impeded, thus preventing reactions in that area. Examples of some suitable shapes are spheres, tablets, extrudates, rings, and honeycomb catalyst monoliths. Various factors influence the choice of which shaped center to use, including ease of coating it with layered catalytic carrier material, and the amount of specific and geometric surface area which the chosen geometric shape delivers.

Fixed bed catalytic systems in general should contain catalyst particles arranged such that there will be no pressure drop problem during the reaction, while simultaneously preventing "channeling" of reactants through the catalyst bed. Suitable catalyst shapes and sizes will depend on the particular reactor used. For most commercial fixed bed processes (excluding honeycomb catalyst monoliths) sizes from about $\frac{1}{8}''$ to $\frac{3}{8}''$ in average diameter will be used, although this size range can vary widely. Considerable latitude is available in determining the size of the impeded center, limited by a minimum size necessary for a fixed bed system. The impeded center and the covering layer combined should approximately equal the size desired for the finished fixed bed catalyst. Impeded centers of particulate, non-monolithic catalysts, (for example, spherical), should have average diameters in the range of about 1 mm to about 10 mm. The impeded center, considered by itself, should be large enough to deliver a packed, bulk geometric (external) surface area in the range of about 2-50 $cm^2/cm^3$, (including honeycomb catalyst monoliths). The extreme values in this range correspond to spherical centers. Monolithic centers tend to show geometric surface areas toward the middle of the range (about 25 $cm^2/cm^3$ for a 400 hole/$in^2$ variety). In the case where the impeded center is a honeycomb catalyst monolith, the center should be formed into a size and shape so that the finished catalyst slides freely into the usual fixed bed reactor tube, while filling the reactor chamber well enough to prevent significant channeling of reactants between the catalyst and the wall. Holes in the honeycomb lattice of the finished catalyst should parallel the reactor tube axis. Suitably any honeycomb adequate for a fixed bed system may be used. Preferred honeycombs are those with about 100 to 800 holes per square inch of cross-sectional area.

The use of material inert to oxychlorination reactions having a low specific surface area is a convenient method of sealing the interior region of the catalyst from availability to the oxychlorination reaction. A suitable range for low specific surface areas would be less than 50 $m^2/g$, but more preferably the specific surface area should be less than 25 $m^2/g$. The invention is also effective when the center material has a low porosity and is even more effective when the center material has both a low specific surface area and a low porosity. The latter is extremely advantageous since it creates an impeded center that eliminates reactions due to both the absence of catalytic sites and the substantial exclusion of reagents. Representative, but nonexhaustive examples of materials suitable for the impeded center are glass, quartz, clay, metal, plastics, magnesia alumina, silica alumina, alpha alumina, silica, or bauxite. In the case of substances such as clay, silica alumina, or silica, similar material may be used for the layered catalytic carrier as long as the impeded center is made substantially inaccessible to the reactants, and/or the active catalytic agent.

When the impeded center is made of a material of low porosity, instead of or in combination with low surface area, substantially all the pores should be greater than about 150 Angstroms (Å) in diameter, as measured by Brunauer, Emmett and Teller porosymmetry. Most preferably, however, substantially all the pores should be greater than 1000 Angstroms in diameter.

The material used for the layered catalyst carrier material is not critical as long as it is suitable for the oxychlorination reaction and conditions contemplated, and is capable of retaining the catalytic agent in a manner which will create an active site for promoting oxychlorination. In general, any oxychlorination carrier material can be used. Representative but nonexhaustive examples of suitable materials include gamma, eta, or delta aluminas, silica aluminas, titania, silica, niobia, clay, magnesia alumina (spinel), or combinations of the above such as alumina-niobia, silica-titania, and the like.

The carrier material used will have a high specific surface area, in the range of about 50 to about 300 square meters per gram, preferably from about 100 square meters per gram to about 200 square meters per gram ($m^2/g$), when it is dry and not disposed on the impeded center. The thickness of this layer on the impeded center will range from about 0.001 millimeter (mm) to about 1 millimeter, preferably from about 0.005 millimeter to about 0.4 millimeter.

Any catalytic agent for oxychlorination reactions can be used in union with the layered catalytic support material to create active sites in the outer layer which will promote oxychlorination. This catalytic agent may be placed on or dispersed in the layered catalytic support material.

The amount of active catalytic agent used can vary widely. Some factors influencing the quantative amount of catalytic agent used include type of coating material, surface area of the coating, layer thickness and porosity of the coating, and the specific catalytic agent used. In general, a catalytic agent in a range from about 0.01 to about 20% by weight, based on the weight of the finished catalyst will be used, but from about 0.5 to about 15% by weight of the finished catalyst is preferred.

The present invention requires less active catalytic agent per catalyst gram than prior art catalysts, when these active agents are excluded from interior areas. A preferred catalytic agent is copper chloride ($CuCl_2$ or Cupric chloride). Copper chloride will normally comprise from about 0.1 to about 9 weight percent of copper based on the total weight of the finished catalyst. Preferably from about 1 to about 7 weight percent copper based on the total weight of the finished catalyst is used. Optionally, a Group 1 or Group 2 metal salt catalyst modifier such as potassium chloride may be added. Examples of these modifiers are salts of lithium, sodium, potassium, magnesium, calcium, strontium, barium, cesium, or rubidium. The preferred modifier is potassium chloride. Amounts of these metal salts will range from about 0.05 to 1.0 on a molar basis relative to copper. A preferred metal to Cu mole ratio range is about 0.05 to 0.4 respectively. Maintaining this ratio at the optimum value while at the same time varying carrier layer thickness will result not only in superior activity gradation in the reactor but also optimum selectivity to desired product. If desired, however, modifiers may be eliminated, and activity gradation controlled solely by varying layer thickness.

Copper compounds suitable for use as active catalytic agents in oxychlorination reactions are cuprous chloride, cupric chloride, copper oxychloride, copper aluminate, copper titanate, copper niobate, copper silicate, copper nitrate, copper bromide, copper sulfate, or copper oxide, or copper salts of organic acids. Examples of other active catalytic agents known to catalyze oxychlorination reactions useful in the present invention are ferric chloride and manganese chloride.

The catalysts of the instant invention can be prepared by a variety of methods. Normally, the impeded center is immersed in a dispersion of finely divided active carrier material, preferably, while using a center impeded by its low porosity. The coated centers are then removed from the dispersion, dried, and optionally calcined. Additional immersion steps are carried out until the desired shell thickness of carrier material is achieved. When using the immersion method to make this catalyst, preferably, a viscous dispersion is used so that the impeded centers will not be wetted, and a thicker layer is deposited per immersion. The catalyst can also be made by filling the pores of the impeded center with an inert liquid or other inert material, thereby closing this area to the carrier material and/or the catalytic agent.

Methods of applying the catalytic agents themselves to carrier material are well known in catalyst art. Any method not destructive to the impeded center and surrounding carrier can be used. Usually simply immersing the carrier in a suitable solution of the catalytic agent is sufficient. The impregnated solid is then dried and optionally calcined. Alternatively, the carrier may be sprayed with a solution of the catalytic agents. Sequential stepwise applications of catalytic agents are also effective. The active catalytic agent may also be mixed with the coating material. When this method is used, however, a limited amount of carrier coating material should be used so as not to bury the active catalytic agents, and the impeded interior should have low porosity, with substantially all the pores greater than 150 Angstroms (Å) in diameter.

The catalysts of the instant invention may be used under any conditions or in any process suitable for a fixed bed oxychlorination catalyst. Some of the processes which may be used in conjunction with the instant invention are described in U.S. Pat. Nos. 3,867,469; 3,720,723; 3,564,066; 4,025,461; 4,046,821; 3,892,816; Great Britain Patent No. 2,007,522A; and German Patent No. 26 51 974. Also, U.S. Pat. Nos. 4,123,467; 4,206,180; and Great Britain Patent Specifications Nos. 1,548,303; 1,548,304; and 1,104,666.

In the processes taught by these patents or in processes suitable for the catalysts of the instant invention, the organics should be in the vapor phase along with a gaseous source of oxygen and a gaseous source of chlorine, when contact is made with the structured catalyst. The organic reactants used may be alpha olefins in the range of $C_3$ to $C_{16}$, ethylene, or aromatic hydrocarbons. The temperature and pressure conditions used should therefore be adequate to insure this gaseous state. Temperature ranges preferred are from about 220° C. to about 320° C.; most preferably the temperature range is about 250° C. to about 280° C. The pressure is preferably in the range of from about 0.29 pounds per square inch (PSI) to 150 pounds per square inch gauge (PSIG), the lower pressures being used for alpha olefins having from 12 to 16 carbon atoms per molecule. The most preferable reactant is ethylene. A preferable source of chlorine is HCl.

The oxychlorination process contemplated by the instant invention comprises contacting a gaseous mixture of an oxygen source, a chlorine source, and the hydrocarbon with one of the structured catalysts of the instant invention under conditions capable of promoting oxychlorination, and then collecting the chlorinated product. Preferably, the chlorine source is either HCl or a mixture of HCl and $Cl_2$.

In any oxychlorination process for fixed bed catalysts, the unique properties of the structured catalysts of the instant invention may be taken advantage of. For example, setting the modifier metal: copper mole ratio in the preferred range of from about 0.05 to about 0.4, while varying the thickness of the layered catalytic carrier material will achieve optimum catalyst activity gradation in the reaction. Catalysts so prepared are sufficiently resistant to deleterious heat effects on EDC selectivity that a reactor system packed throughout with a single zone of undiluted catalyst will produce commercially attractive production rates and selectivity. Savings in production lost during catalyst changeout would be gained from the speed which a single (instead of a multi-zone) catalyst can be charged. These catalysts also enable the total elimination of modifier which would increase conversion capabilities and result in the elimination of modifier-caused undesirables from the product, while still maintaining some activity gradation (reactor temperature) control by controlling carrier loading.

BRIEF DESCRIPTION OF THE DRAWINGS

FIG. 1 shows a reactor temperature profile for a state of the art catalyst control.

The following examples are presented to illustate the invention and not to limit it. In the examples, all parts and percentages are by weight unless otherwise specified. Example 1 is comparative while the subsequent examples illustrate the present invention.

EXAMPLE 1

A vertical 1" I.D.×4' long nickel reactor was set up to simulate the first of a series of 3 oxychlorination reactors. Silicone oil at ~200° C. was pumped through the reactor jacket in upflow. All tubing exposed to HCl was nickel. All fittings exposed to HCl were monel.

Feed gases were metered to the top of the reactor at 110 psig head pressure. The first ~8.5" of reactor was used as a gas preheater. Reactor temperatures were measured by traveling thermocouple in a central vertical ⅛" O.D. nickel thermowell.

Figure 2:
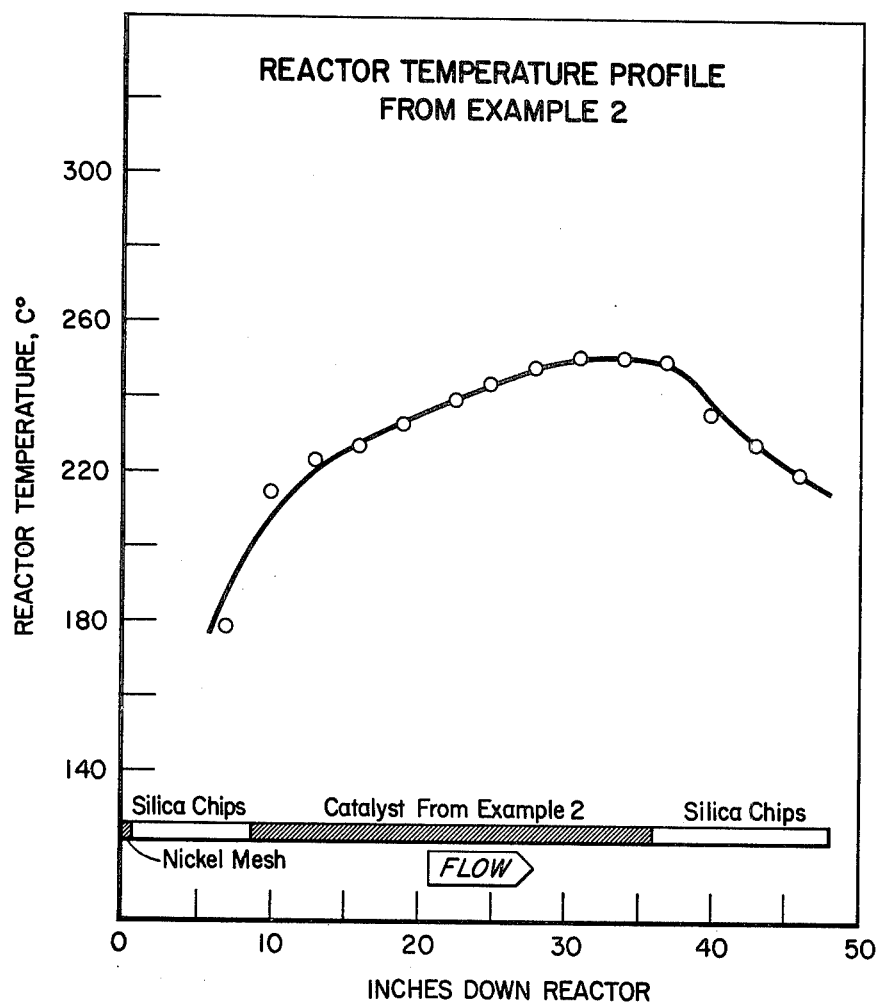
FIG. 2 is a reactor temperature profile showing the effect of surface slurry coating of gamma-alumina on an alpha-alumina center.

The reactor was packed in 2 zones (as shown in FIG. 2) with catalysts made according to U.S. Pat. No. 4,206,180. Catalyst, A, in the top zone was 3-6 mesh gamma alumina spheres impregnated with 5.6% $CuCl_2$ and 2.8 weight percent (w/o) KCl based on the weight of the finished catalyst. Catalyst, B, in the bottom zone was 3-6 mesh gamma (γ) alumina spheres impregnated with a nominal 18 w/o $CuCl_2$ and 1.8 w/o KCl based on the weight of the finished catalyst.

During reaction, the crude liquid contents of a knockout pot were periodically collected, weighed, and analyzed by gas liquid chromatography (glc). A slipstream of offgas from the knock-out pot was scrubbed with dilute caustic solution. Periodic samples of the scrubbed offgas were analyzed by glc for organics. A slipstream of this scrubbed offgas was passed through an oxygen analyzer for measurements of unconverted oxygen.

Table 1 indicates the gas feed rates. FIG. 1 shows the reactor temperature profile under the test conditions. Table 2 summarizes the glc analysis of crude liquid EDC.

EXAMPLE 2

A 615.0 gram (g) sample of ¼" diameter alpha (α)-alumina spheres having a specific surface area of 15.5 $m^2/g$ was saturated with distilled water, drained, and dipped into a dispersion of gamma (γ)-alumina. The dipped spheres were drained and dried on stainless steel screens at 110° C. for 1 hr., then calcined 1 hour at 400° C.

The cooled spheres were rewet with distilled water, redipped in the γ-alumina dispersion, redried at 110° C. for 1 hour, and calcined at 500° C. for 3 hours to produce 654.0 g of coated spheres.

A 230.0 g sample of these coated spheres was impregnated with a 90 milliliters (ml) solution of 33.6 g of $CuCl_2.2H_2O$ and 8.8 g of KCl in distilled water over 30 minutes. The spheres were drained and then dried at 170° C. for about 16 hours to produce 262.0 g of tantinged magenta spheres. Analyses of these spheres showed 4.40 w/o Cu, 1.72 w/o K, 5.95 weight percent (w/o) $Cl^-$, and 475 parts per million (ppm) Fe. Surface area of the finished catalyst was about 14.5 $m^2/g$. and the $\gamma-Al_2O_3$ coating was about 5.2 wt.% of the total catalyst.

The reactor was packed with these spheres as indicated in FIG. 2. The spheres were tested under the same conditions as in Example 1. Analytical results from the crude liquid EDC are shown in Table 2. The reactor thermal profile is shown in FIG. 2.

EXAMPLE 3

To a 230 g sample of ¼" diameter α-alumina spheres having a specific surface area of 15.5 $m^2/g$ was added a 360 ml solution of 240.0 g of $Al(NO_3)_3.9H_2O$ in distilled water. After 15 minutes, the excess liquid was drained and bottled. The spheres were dried overnight at 170° C. and then calcined for 2 hours at 500° C. to yield 237.4 g of coated spheres.

These spheres were resoaked in the $Al(NO_3)_3$ solution for 15 minutes. The excess solution was rebottled. The spheres were re-dried at 170° C. and then calcined for 2 hours at 500° C. to yield 247.2 g of coated spheres.

These spheres were similarly resoaked in the $Al(NO_3)_3$ solution, drained, dried, and calcined in 4 more cycles to yield 286.5 g of coated spheres.

A 266.5 g sample of the coated spheres was impregnated by soaking with a 147 ml solution of 78.0 g of $CuCl_2.2H_2O$ and 20.48 g of KCl in distilled water for 10 minutes. The spheres were drained and dried overnight at 170° C. to yield 307.9 g of mainly tan spheres. Analyses showed that these spheres contained 4.29 w/o Cu, 1.60 w/o K, 5.45 w/o $Cl^-$, and 270 ppm Fe. Surface area was 10.4 $m^2/g$ and $\gamma-Al_2O_3$ coating was about 17.1 wt% of the total catalyst.

Figure 3:
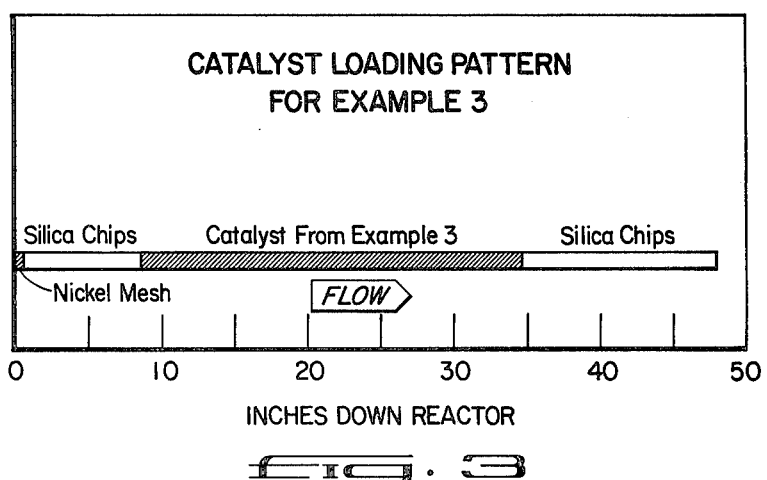
FIG. 3 is a catalyst loading profile for a reactor.

The spheres were charged into the test reactor as shown in FIG. 3 and tested under the conditions of Example 1. Glc data on the crude liquid EDC product are indicated in Table 2. A broad reactor hotspot (285° C.) was located at the bottom of the catalyst zone.

EXAMPLE 4

A 230.0 g sample of ¼" diameter α-alumina spheres having a specific surface area of 15.5 $m^2/g$ was soaked 5 minutes in a 836 ml solution of 800 g of $Al(NO_3)_3.9H_2O$ in distilled water. Excess liquid was drained and bottled. The drained spheres were dried for 2 hours at 170° C. and then calcined for 2 hours at 500° C. to yield 241.6 g of coated spheres.

These spheres were resoaked, dried, and calcined through 5 more cycles to yield 309.4 g of coated spheres.

A 292.1 g sample of the coated spheres was impregnated with a 143 ml solution of 85.5 g of $CuCl_2.2H_2O$ and 22.4 g of KCl in distilled water for 5 minutes. The spheres were drained and then dried overnight at 170° C. to yield 332.4 g of mainly tan spheres. Analyses showed that these spheres contained 3.90 w/o Cu, 1.45 w/o K, 5.28 w/o $Cl^-$, 110 ppm $NO^-_3$, and 180 ppm Fe. Surface area was about 5.3 $m^2/g$ and the $\gamma-Al_2O_3$ coating was about 22.6% by wt. of the finished catalyst.

Figure 4:
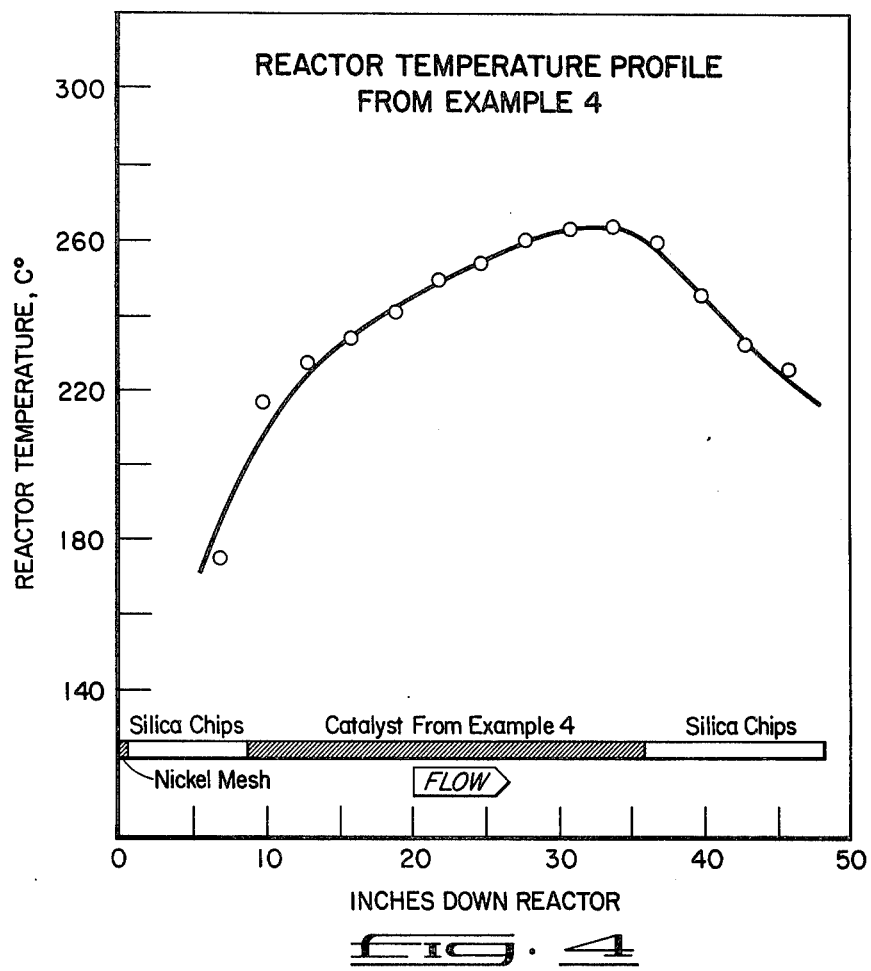
FIG. 4 is a reactor temperature profile showing an increased gamma-alumina coating using alumina nitrate techniques.

These spheres were charged into the test reactor and tested under the conditions of Example 1. Glc data on the crude liquid EDC product are listed in Table 2. The reactor temperature profile is shown in FIG. 4.

TABLE 1

| | TEST CONDITIONS | | | | | | |
|---|---|---|---|---|---|---|---|
| | Gas Feeds, moles/hr. | | | | % $O_2$ | Crude Liquid,g/hr | |
| Example # | $O_2$ | HCl | $C_2H_4$ | $N_2$ | Conv. | EDC | $H_2O$ |
| 1 | 4.0 | 18.4 | 56.7 | 98 | 97 | 518.0 | 170.1 |
| 2 | 4.0 | 18.4 | 56.7 | 98 | 34 | 94.3 | 60.8 |
| 3 | 4.0 | 18.4 | 56.7 | 98 | 62 | 320.1 | 130.2 |
| 4 | 4.0 | 18.4 | 56.7 | 98 | 51 | 187.2 | 94.6 |

TABLE 2

Glc DATA FROM CRUDE LIQUID EDC NORMALIZED TO EXCLUDE $C_2H_4$

| Organic Components, Mole Percent | Example 1 | Example 2 | Example 3 | Example 4 |
|---|---|---|---|---|
| Vinyl Chloride | 0.0734 | 0.0808 | 0.0046 | 0.0035[c] |
| Ethyl Chloride (undesired) | 0.7386 | 0.1257 | 0.1237 | 0.0759[c] |
| trans-Dichloroethylene | 0.1342 | 0.1631 | 0.1907 | 0.1545 |
| Carbon Tetrachloride (desired) | 0.0722 | 0.5923 | 0.3622 | 0.3342 |
| Trichloroethylene[a] | 0.1617 | 0.1778 | 0.2166 | 0.2138 |
| Chloroform[a] | 0.0370 | 0.0409 | 0.0496 | 0.0489 |
| cis-Dichloroethylene[a] | 0.0139 | 0.0153 | 0.0186 | 0.0184 |
| Ethylene Dichloride (desired) | 98.6828 | 98.5740 | 98.9767 | 99.0462 |
| 1,1,2-Trichloroethane | 0.0289 | 0.0259 | 0.0245 | 0.0239 |
| Chloral | 0.0000 | 0.0000 | 0.0000 | 0.0000 |
| 2-Chloralethanol | 0.0000 | 0.0000 | 0.0000 | 0.0000 |
| Unknown[b] | (0.0573 | 0.2042 | 0.0328 | 0.0809) |

[a]Chart traces ordinarily show cis-dichloroethylene and chloroform shoulders estimated to be 5–10% each of the peak area computer-integrated as trichloro-ethylene.
[b]Assumed to have molecular weight of 100 and glc response factors identical to that of ethylene dichloride.
[c]Combined peak was assumed to contain VCM similar to that in Example 3.

EXAMPLE 5

To indicate activity and the effectiveness of the α-$Al_2O_3$ impeded centers, a $CuCl_2$ catalyst on α-$Al_2O_3$ spheres, was prepared as follows:

500 ml of ¼"α-$Al_2O_3$ spheres (same as used for the impeded centers in Examples 2–4) were soaked overnight in a solution of 124.7 g of $CuCl_2.2H_2O$ and 19.8 g of KCl in 400 ml of distilled water in a covered beaker. The drained spheres were then dried for 2 hours at 160° C. to yield a catalyst with the following properties:
specific surface area = 21.0 m²/g
weight percent Cu = 4.77
weight percent K = 0.94
weight percent $Cl^-$ = 5.43
K:Cu molar ratio = 0.32

The previously described reactor was charged with a 36" zone of this catalyst, and was heated to 200° C., as usual, fed with 12.7 moles/hr of ethylene, 11.8 moles/hr of HCl, 2.4 moles/hr of $O_2$, and 107 moles/hr of $N_2$. The catalyst was inactive. For the catalyst described in Example 1, these conditions were sufficient to generate 304° C. hotspot temperature and 97% $O_2$ conversion.

DISCUSSION OF EXAMPLES

Examples 1 through 4 and FIGS. 1 through 4 taken comparatively show that the catalysts of the present invention have superior selectivity to carbon tetrachloride and ethylene di-chloride. Lower amounts of the undesired ethyl chloride are also shown relative to the conventional catalysts of Example 1. (See mole percent data in Table 2)

Since the structured catalysts' activity may be controlled by varying the coating of thickness, the modifiers used in Examples 2 through 4 are not necessary. Catalyst activity is controllable by varying the added parameters not available in conventional catalysts. More specifically this is achieved by varying the coating thickness via carrier loading in conjunction with the particular impeded center involved. With regard to the specific catalysts involved in Examples 2 through 4, an added benefit is achieved in eliminating the potassium modifier. With lower potassium concentrations in the catalysts, the production of undesired potassium-caused impurities would decrease. Such impurities are, for example, transdichloroethylene, trichloroethylene, chloroform, and cis-dichloroethylene.

Another capability demonstrated by the examples given is a more moderate temperature gradation in the reactor. (See FIGS. 1, 2 and 4.) These data compare the conventional catalysts of Example 1 and the structural catalysts depicted in Examples 2 through 4, and indicate that reactor temperature can be more evenly distributed, if desired, through the use of structured catalysts without adversely affecting catalyst selectivity.

Figure 5:
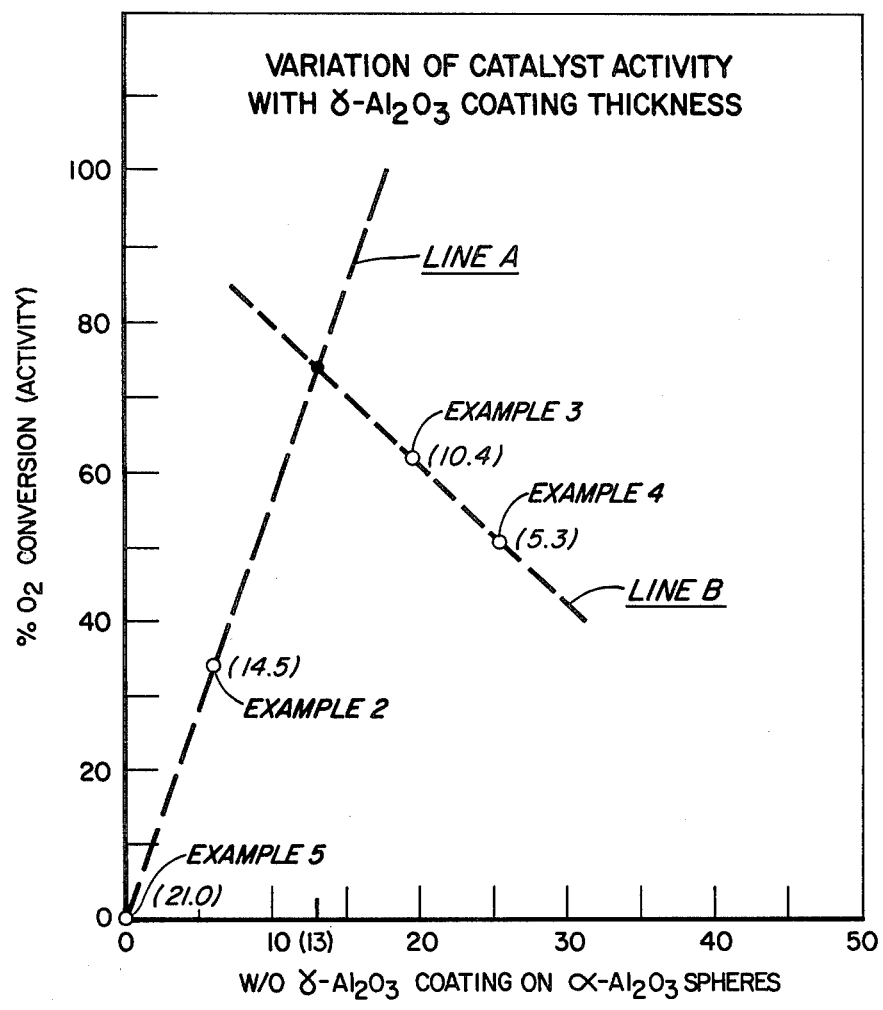
FIG. 5 shows the variation of catalyst activity dependent on gamma-alumina coating thickness.

FIG. 5 demonstrates the effects of these structured catalysts on activity. In these reactions oxygen was the limiting reactant so activity is expressed in terms of percent oxygen conversion. Note that values in parenthesis on FIG. 5 represent the corresponding values of specific surface area in meters squared per gram (m²/g).

The catalytic activity of the structured catalysts depicted in FIG. 5 was due to the gamma-alumina ($\gamma$-$Al_2O_3$) and active catalytic agent $CuCl_2$ with KCl modifier. This is demonstrated by the fact that no activity was shown where there was no gamma-alumina coating. (See FIG. 5-0% gamma-$Al_2O_3$ and 0% activity for the catalyst described in Example 5.)

The two distinct characteristics of this coating (carrier) material that influenced the oxygen conversion (activity) of this particular system were: (1) the amount, and, hence, thickness of the gamma $Al_2O_3$, and (2) the resulting specific surface area of the catalysts surface after the coating was affixed to it (given on FIG. 5). Coating thickness has a stronger influence for the values found along line A. Line B indicates that at a certain point the loss of surface area, occurring simultaneously with increasing amounts of layered catalytic material will become the stronger influence and cause activity to decrease. This is probably due to the filling of large pores. Of course, the point intersection of these two lines will be different for each separate system since the characteristics of different materials and the characteristics of their inter-related state will change and will influence both porosity and specific surface area of the resulting structured catalyst. For the system disclosed in Examples 2 through 4 and depicted in the pertinent Figures, the maximum activity that may be expected is at approximately 13% gamma-$Al_2O_3$ coating. For that point, the percent conversion would be expected to be at around 74%. It is naturally expected that if the KCl modifier were eliminated, that the point of maximum conversion would increase considerably, most probably to nearly 100% conversion at even less gamma Al₂O₃ coating. The beneficial use achieved by recognition of the nature of this relationship is that reactor activity may be specifically planned. For example, since catalyst activity can be planned, catalyst batches of varying activity can be prepared by changing the loading amounts of the layered carrier. Thus the thickness of the active coating would change. For a 3 zone system, if our structured catalysts were used, a less active catalyst is prepared for an initial zone, an intermediately active catalyst for a central zone, and the most active catalyst for the finishing reactor zone. This is achieved by varying the combined parameters delivered exclusively by the catalysts of this invention. Thus, one can tailor a fixed bed oxychlorination catalyst for individual circumstances and desires.

While certain details have been shown for the purposes of illustrating this invention, it will be apparent to those skilled in this art that various changes and modifications may be made herein without departing from the script or scope of the invention.

Having described our invention, what we desire to secure by Letters Patent are:

We claim:

1. A structured catalyst for oxychlorination of ethylene, alpha olefins, and aromatics, comprising:
   (a) an impeded center which prevents oxychlorination reactions by the exclusion of active catalytic sites said impeded center having a porosity such that substantially all of the pores are greater than about 150 Angstroms in diameter;
   (b) a layer of catalyst carrier material disposed on the impeded center of (a) in a thickness of from about 0.001 millimeters to about 1 millimeter, said catalyst carrier material which has, when dry and prior to placement on the center, a specific surface area of from about 50 to about 300 square meters per gram, and
   (c) an oxychlorination agent in a range of from about 0.01 to about 20 percent by weight of the total finished catalyst supported by (b).

2. A structured catalyst as specified in claim 1 wherein:
   a layer of catalyst carrier material selected from the group consisting of a clay, gamma alumina, eta alumina, delta alumina, silica, silica-alumina, titania, niobia, or magnesia-alumina.

3. A structured catalyst as specified in claim 2 wherein:
   the catalytic agent is selected from the group consisting of cupric chloride, cuprous chloride, copper oxychloride, copper aluminate, copper titanate, copper niobate, copper silicate, copper oxide, copper sulfate, copper salts of organic acids, copper nitrate, copper bromide, ferric chloride, or manganese chloride.

4. A structured catalyst as described in claim 3 wherein:
   the impeded center is made of material selected from the group consisting of glass, quartz, metal plastics, bauxite or alpha alumina.

5. A structured catalyst as described in claim 3 wherein:
   the impeded center is inaccessible to reactants or contains no active catalytic sites, and is made of material selected from the group consisting of clay, silica, silica-alumina, or magnesia alumina.

6. A structured catalyst for oxychlorination of ethylene, alpha olefins, and aromatics, comprising:
   (a) an impeded center which prevents oxychlorination reactions by the exclusion of active catalytic sites, said impeded center having a specific surface area less than 50 square meters per gram, and having a porosity such that substantially all of the pores are greater than 150 Angstroms in diameter,
   (b) a layer of catalyst carrier material disposed on the impeded center of (a) in a thickness of from about 0.001 mm to about 1 mm, said catalyst carrier material having, when dry and prior to placement on the center, a specific surface area in the range of from about 50 to about 300 square meters per gram, and
   (c) a catalytic agent for oxychlorination disposed on the layer of catalyst carrier material in an amount that said catalytic agent is present in a concentration of from about 0.01 to 20 percent by weight of the finished catalyst, said catalytic agent being cupric chloride, cuprous chloride, copper oxychloride, copper nitrate, copper bromide, copper aluminate, copper titanate, copper niobate, copper silicate, copper oxide, copper sulfate, or copper salts of organic acids, and
   (d) a salt of lithium, sodium, potassium, magnesium, calcium, strontium, barium, rubidium, or cesium is disposed on the structured catalyst after (c), in an amount that leaves a metal to copper mole ratio in the range of from about 0.05 to 1.0.

7. A catalyst as specific in claim 6 wherein:
   the impeded center is a honeycomb catalyst monolith.

8. A structured catalyst as specified in claim 6 wherein:
   the impeded center is made of material selected from the group consisting of glass, quartz, metal, plastics, bauxite or alpha alumina.

9. A structured catalyst as described in claim 6 wherein:
   the impeded center is inaccessible to reactants or the active catalytic agent and is selected from the group consisting of clay, silica, silica-alumina, or magnesia-alumina.

* * * * *